(12) United States Patent
Liphardt et al.

(10) Patent No.: US 7,317,530 B2
(45) Date of Patent: *Jan. 8, 2008

(54) COMBINED SPATIAL FILTER AND RELAY SYSTEMS

(75) Inventors: Martin M. Liphardt, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 301 days.

This patent is subject to a terminal disclaimer.

(21) Appl. No.: 11/085,450

(22) Filed: Mar. 22, 2005

(65) Prior Publication Data

US 2006/0268271 A1   Nov. 30, 2006

Related U.S. Application Data

(63) Continuation-in-part of application No. 10/928,429, filed on Aug. 27, 2004.

(60) Provisional application No. 60/498,479, filed on Aug. 28, 2003, provisional application No. 60/576,466, filed on Jun. 3, 2004.

(51) Int. Cl.
    *G01J 4/00* (2006.01)

(52) U.S. Cl. ...................................... 356/369
(58) Field of Classification Search ................ 356/317, 356/369
See application file for complete search history.

(56) References Cited

U.S. PATENT DOCUMENTS

| | | | |
|---|---|---|---|
| 3,748,015 A | 7/1973 | Offner | 359/366 |
| 5,608,526 A | 3/1997 | Piwonka-Corle et al. | 356/369 |
| 5,859,424 A * | 1/1999 | Norton et al. | 250/226 |
| 5,910,842 A | 6/1999 | Piwonka-Corle et al. | 356/369 |
| 5,917,594 A | 6/1999 | Norton | 356/327 |
| 6,545,758 B1 * | 4/2003 | Sandstrom | 356/317 |
| 6,587,282 B1 * | 7/2003 | Wang et al. | 359/797 |
| 6,734,967 B1 | 5/2004 | Piwonka-Corle et al. | 356/369 |
| 2002/0101587 A1 * | 8/2002 | Wilson et al. | 356/328 |
| 2005/0286047 A1 * | 12/2005 | Boege | 356/317 |

FOREIGN PATENT DOCUMENTS

WO   WO 2005/077135 A2   8/2005

* cited by examiner

*Primary Examiner*—Tarifur Chowdhury
*Assistant Examiner*—Isiaka O Akanbi
(74) *Attorney, Agent, or Firm*—James D. Welch

(57) ABSTRACT

Low aberration relay systems modified to perform as spatial filters in reflectometer, spectrophotometer, ellipsometer, polarimeter and the like systems.

27 Claims, 9 Drawing Sheets

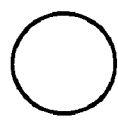
FIG. 6a
FIG. 6B
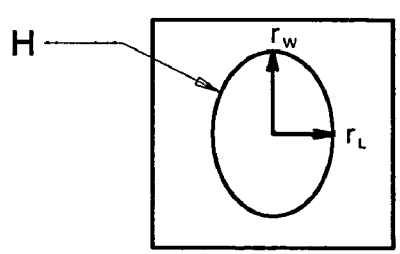
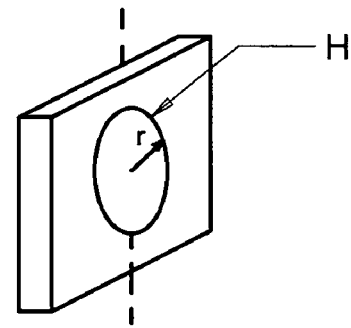
FIG. 6c
FIG. 6d

COMBINED SPATIAL FILTER AND RELAY SYSTEMS

This application is a CIP of application Ser. No. 10/928,429, filed Aug. 27, 2004 and therevia claims benefit of Provisional Application 60/498,479 Filed Aug. 28, 2003. Further, benefit of Provisional Application Ser. No. 60/576,466 filed Jun. 3, 2004 is claimed directly.

TECHNICAL FIELD

The disclosed invention relates to spatial filters, and more particularly to low aberration relay systems modified to perform as spatial filters.

BACKGROUND

It is known in the art to focus a broadband beam of electromagnetic radiation onto a small spot in ellipsometers by reflective or refractive optics. Typically, said prior art systems image a small aperture onto a spot on a sample with high demagnification, and suffer from varying degrees of optical aberrations, (eg. spherical, chromatic, astigmatism etc.). Further, surfaces of mirrors can be non-ideal as a result of non-traditional manufacturing of special optics. Further, the cost of non-spherical optics is high.

It is also known that spherical optics can be fashioned to relay an objective with 1:1 magnification and with essentially no aberrations. Expired U.S. Pat. No. 3,748,015 describes such a relay system comprising two elements:

a) a concave spherical mirror; and c) a convex spherical mirror;

said elements being arrange such that electromagnetic radiation caused to approach the concave spherical reflects at a first location thereon is reflected to said a convex spherical mirror, from which it reflects onto a second location of said concave spherical mirror, from which it reflects as a converging beam of electromagnetic radiation if the electromagnetic radiation caused to approach the concave spherical mirror at a first location was, for instance, a point source. FIG. 1 of this disclosure demonstrates a 015 Patent System.

Patents which describe reflective optics in ellipsometer systems are U.S. Pat. Nos. 6,734,967; 5,910,842 and 5,608,526 to Piwonka-Corle et al. The 526 Patent is the earliest thereof to describe use of all-reflective focusing elements in an ellipsometer. Patents to Norton, U.S. Pat. Nos. 5,859,424 and 5,917,594 are disclosed as they describe use of an apodizing filter to decrease beam spot size on a sample, and use of a negative miniscus lens to correct for spherical abberations where a spherical mirror is present in the path of an electromagnetic beam.

The disclosed invention applies the system of the expired 015 Patent in reflectometer, spectrophotometer, ellipsometer, polarimeter and the like systems, variously combined with spatial filters.

DISCLOSURE OF THE INVENTION

One embodiment of the disclosed invention is a combined spatial filter and relay system comprises three elements:

a) a concave spherical mirror having at least one concave spherical surface and an aperture hole therethrough;

b) a flat mirror; and c) a convex spherical mirror having at least one convex spherical surface.

Said elements are arranged such that electromagnetic radiation caused to approach the concave spherical mirror passes through said aperture hole and reflects from said flat mirror onto a first location of a concave surface of said concave spherical mirror. It then reflects from said first location onto a convex spherical surface of said convex spherical mirror and reflects therefrom onto a second location of said concave surface of said concave spherical mirror from which it reflects as a converging beam of electromagnetic radiation.

A second embodiment of the disclosed combined spatial filter and relay system comprises:

a) an aperture;

b) a flat mirror;

c) a concave spherical mirror having at least one concave spherical surface; and d) a convex spherical mirror having at least one convex spherical surface.

Said elements are arranged such that electromagnetic radiation which relay said aperture is caused to approach the flat mirror and reflect therefrom onto a first location of a concave surface of said concave spherical mirror. It then reflects from said first location onto a convex spherical surface of said convex spherical mirror and reflects therefrom onto a second location of said concave surface of said concave spherical mirror from which it reflects as a converging beam of electromagnetic radiation.

Said embodiment can include a second flat mirror positioned to intercept and reflect electromagnetic radiation reflected from said second location of said concave surface of said concave spherical mirror as a converging beam of electromagnetic radiation. Said modified second embodiment then comprises five elements:

a) an aperture;

b) a first flat mirror;

c) a concave spherical mirror having at least one concave spherical surface;

d) a convex spherical mirror having at least one convex spherical surface; and e) a second flat mirror.

Said elements are arranged such that electromagnetic radiation from said aperture is caused to approach the first flat mirror and reflect therefrom onto a first location of a concave surface of said concave spherical mirror. Said beam reflects from said first location onto a convex spherical surface of said convex spherical mirror and reflects therefrom onto a second location of said concave surface of said concave spherical mirror from which it reflects onto said second flat mirror which is positioned to intercept and reflect electromagnetic radiation reflected from said second location of said concave surface of said concave spherical mirror, as a converging beam of electromagnetic radiation.

In ellipsometry applications it is best to keep the angle of incidence of electromagnetic radiation onto a flat mirror low, (eg. less than 20 degrees). Where it is desired to use a larger angle, say 45 degrees, the presently disclosed invention can be advantageously modified. An example is a system for investigating a sample comprising:

a source of electromagnetic radiation;

an aperture;

first and second relay systems, each thereof comprising four elements:

a) a first flat mirror;
b) a concave spherical mirror having at least one concave spherical surface;
c) a convex spherical mirror having at least one convex spherical surface; and
d) a second flat mirror.

Said elements are arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror, which is positioned to intercept and reflect electromagnetic radiation reflected from said second location of said concave surface of said concave spherical mirror as a converging beam of electromagnetic radiation;

and a detector;

said sample being positioned between said first and second relay systems.

Said first relay system is positioned to relay electromagnetic radiation from the source thereof as it passes through said aperture, and direct it onto a surface of said sample at an oblique angle of incidence, and said second relay system is positioned to receive electromagnetic radiation reflected from the sample and pass it on to said detector, the propagation direction of electromagnetic radiation entering and exiting each of said first and second relay systems being substantially unchanged by passing therethrough.

Said system is further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

(It is noted that while said first and second flat mirrors are typically oriented so that a beam of electromagnetic radiation approaches along a 45 degree Angle-of-Incidence, the present invention is not limited to such a configuration. That is, the Angle-of-Incidence can be any functional angle, where compensating adjustments are made in FIGS. 5a and 5b to effect an intended Angle-of-Incidence of the beam of electromagnetic radiation where it impinges on the Surface of a sample).

A modified system for investigating a sample comprises:

a source of electromagnetic radiation;

an aperture;

first and second relay systems, each thereof comprising four elements:
a) a first flat mirror;
b) a concave spherical mirror having at least one concave spherical surface;
c) a convex spherical mirror having at least one convex spherical surface; and
d) a second flat mirror;

said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror, from which it reflects onto said second flat mirror which is positioned to intercept and reflect electromagnetic radiation reflected from said second location of said concave surface of said concave spherical mirror, as a converging beam of electromagnetic radiation;

and a detector;

said first and second relay systems being positioned on the same side of the sample;

the propagation direction of electromagnetic radiation entering and exiting each of said first and second relay systems being substantially unchanged by passing therethrough;

said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

Said system for investigating a sample can further comprises:
a) a polarizer between said source and sample; and
b) an analyzer between said sample and detector;

and constitute an ellipsometer, and if a compensator is present between said source and detector, a polarimeter results.

An additional embodiment of a system for investigating a sample comprises:

a source of electromagnetic radiation;

an aperture;

a relay system comprising three elements:
a) a flat mirror;
b) a concave spherical mirror having at least one concave spherical surface;
c) a convex spherical mirror having at least one convex spherical surface;

said elements being arranged such that electromagnetic radiation is caused to approach the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation;

a sample; and a detector.

Said aperture can be in said concave spherical mirror.

Said system for investigating a sample can further comprise:
a) a polarizer between said source and sample; and
b) an analyzer between said sample and detector;

thereby providing an ellipsometer.

There can further be present at least one compensator between said source and detector.

In any of the systems disclosed above, a coating can be present on the surface of at least one present element, (eg. concave, convex, first flat, second flat mirror etc. to change the intensity vs. wavelength plot of a reflected electromagnetic beam relative to an incident beam.

Finally, in any of the systems disclosed above said aperture can be circular or actually or effectively non-circular.

The disclosed invention will be better understood by reference to the Detailed Disclosure Section of this Specification, in combination with the Drawings.

SUMMARY OF THE INVENTION

It is a primary purpose and/or objective of disclosed invention to teach combined spatial filter and reflective relay systems.

It is another purpose and/or objective of disclosed invention to teach combined spatial filter and reflective relay systems in reflectometer, spectrophotometer, ellipsometer, polarimeter and the like systems.

It is another purpose and/or objective of disclosed invention to teach application of 1:1 reflective relay systems as taught in expired U.S. Pat. No. 3,748,015, in reflectometer, spectrophotometer, ellipsometer, polarimeter and the like systems.

Other purposes and/or objectives of disclosed invention will become apparent upon a reading of the specification and claims.

BRIEF DESCRIPTION OF THE DRAWINGS

FIGS. 6a and 6b demonstrate how a Circular Beam (in cross-section), appears when impinged onto the Surface of a Sample at an oblique Angle-of-Incidence.

FIGS. 6c and 6d demonstrate non-circular Apertures which offset the effect shown in FIG. 6b.

DETAILED DESCRIPTION

Figure 1:
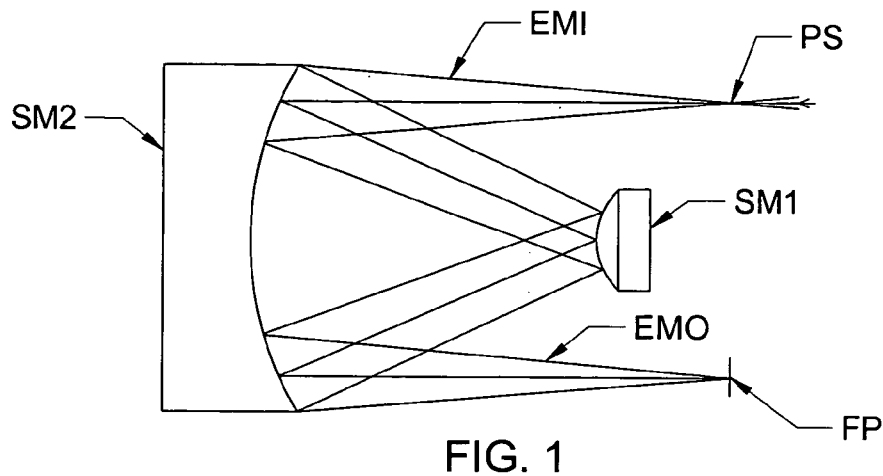
FIG. 1 shows a prior art 1:1 relay system.

Turning now to FIG. 1, there is shown a system disclosed in expired U.S. Pat. No. 3,748,015. Indicated is a relay system comprising two elements:
 a) a concave spherical mirror (SM2); and
 c) a convex spherical mirror (SM1).

Said elements (SM2) and (SM1) are arrange such that electromagnetic radiation (EM1) caused to approach the concave spherical mirror (SM2) reflects at a first location thereon, and is reflected to said a convex spherical mirror (SM1), from which it reflects onto a second location of said concave spherical mirror (SM2), from which it reflects as a beam of electromagnetic radiation (EMO) with an image point (FP), if the electromagnetic radiation (EMI) which is caused to approach the concave spherical mirror (SM2) at a first location thereon was, for instance, an equivalent to a point source (PS). The 015 Patent describes the focal length of the concave spherical mirror (SM2) and being twice the focal length of the convex spherical mirror (SM1).

Figure 2A:
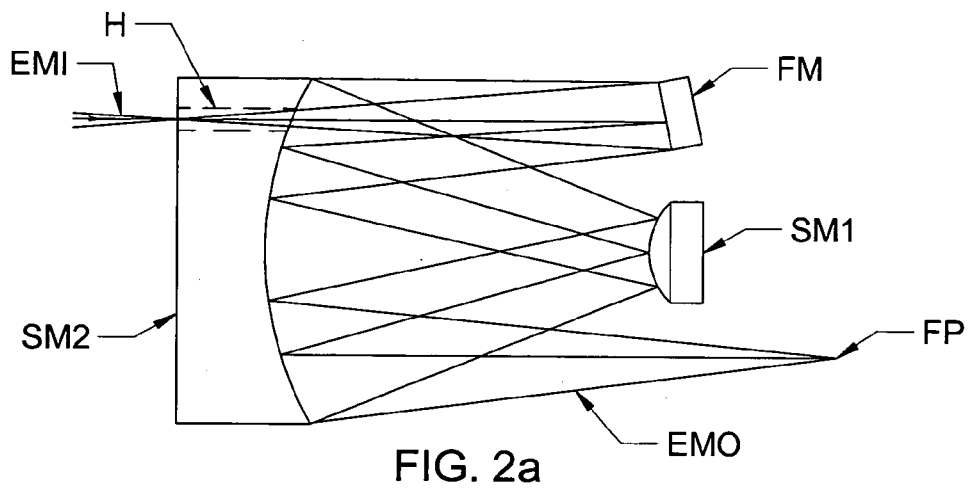
FIG. 2a shows a first embodiment of a combined present invention spatial filter and relay system.

FIG. 2a shows a combined spatial filter and relay system comprising three elements:
 a) a concave spherical mirror (SM2) having at least one concave spherical surface and an aperture hole (H) therethrough;
 b) a flat mirror (FM); and
 c) a convex spherical mirror (SM1) having at least one convex spherical surface.

Said elements are arranged such that electromagnetic radiation (EM1) caused to approach the concave spherical mirror (SM2) passes through said aperture hole (H) and reflects from said flat mirror (FM) onto a first location of a concave surface of said concave spherical mirror (SM2), then reflects from said first location onto a convex spherical surface of said convex spherical mirror (SM1) and reflects therefrom onto a second location of said concave surface of said concave spherical mirror (SM2) as a converging beam of electromagnetic radiation. Note that the electromagnetic radiation approaches the Concave Mirror (SM2) from "back" side thereof. Said "back" side can be of any functional shape, but is shown as being flat for demonstrative purposes.

Figure 2B:
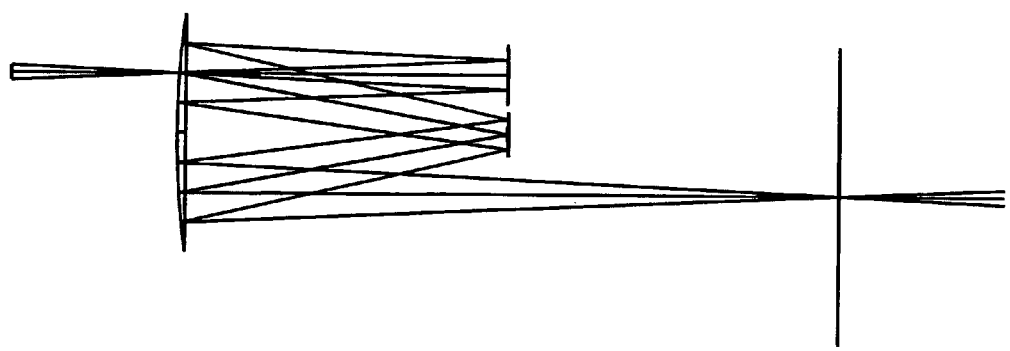
FIGS. 2b-2e show ray traces of how the FIGS. 1 and 2a system effects beams with various characteristics.
Figure 2C:
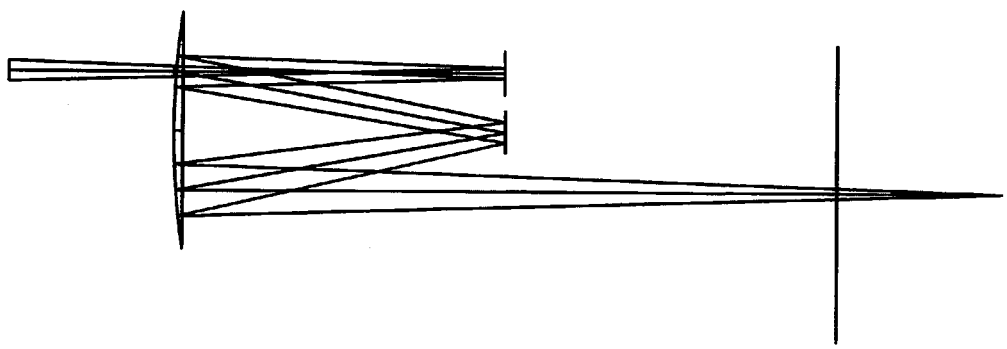
Figure 2D:
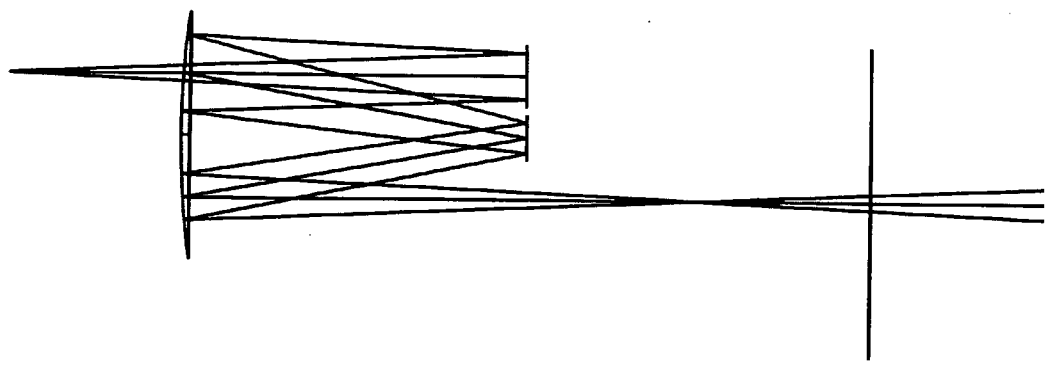
Figure 2E:
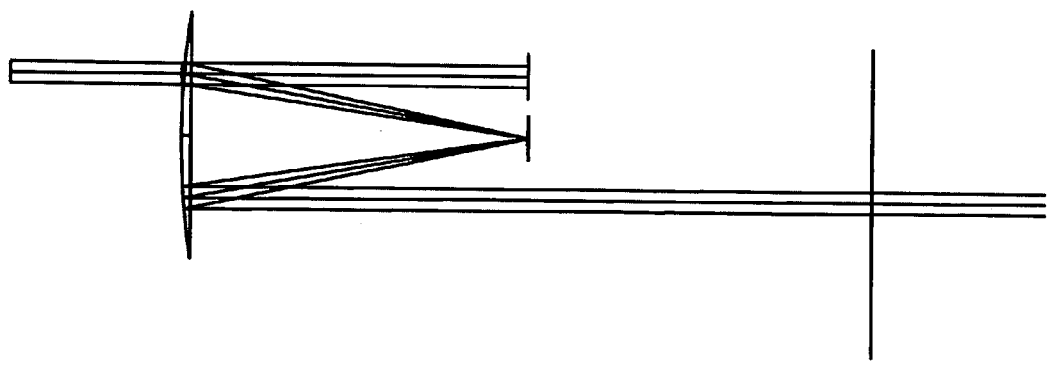

For insight, FIGS. 2b-2e show ray traces of how the FIG. 2a system effects beams with various characteristics. FIG. 2b shows a rays equivalent to those in FIG. 2a. FIGS. 2c and 2d show an effective point source of a beam need not be at the Spatial Filter (H), and FIG. 2e demonstrates the use of a collimated beam in a FIG. 1 system, and the relay value of the system.

Figure 3:
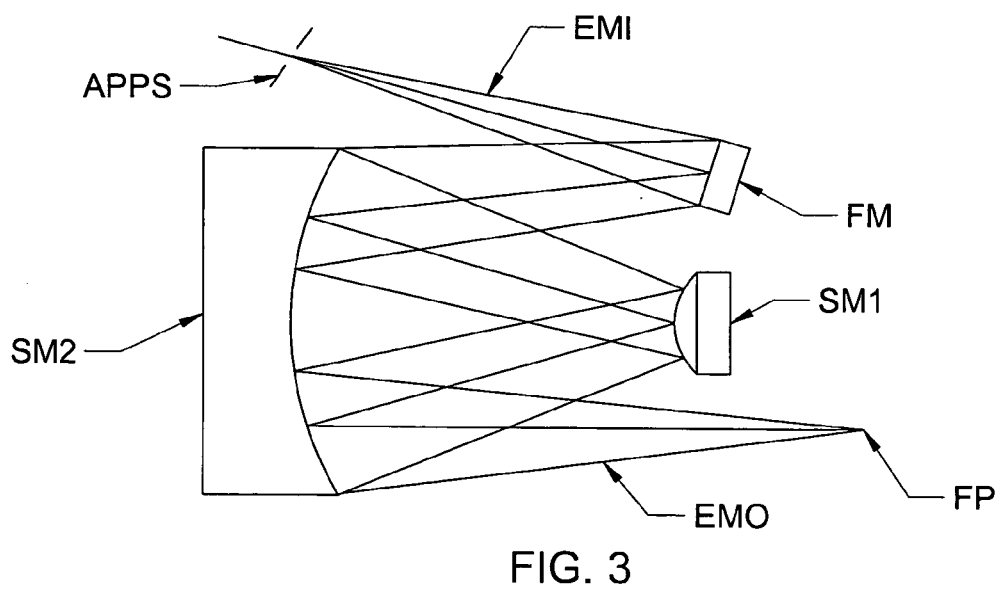
FIG. 3 shows a second embodiment of a combined present invention spatial filter and relay system.

FIG. 3 shows a present invention combined spatial filter and relay system comprising:
 a) an aperture (APPS);
 b) a flat mirror (FM);
 c) a concave spherical mirror (SM2) having at least one concave spherical surface; and
 d) a convex spherical mirror (SM1) having at least one convex spherical surface.

Said elements are arranged such that electromagnetic radiation (EMI) from said aperture (H) is caused to approach the flat mirror (FM) and reflect therefrom onto a first location of a concave surface of said concave spherical mirror (SM2), reflect from said first location onto a convex spherical surface of said convex spherical mirror (SM1) and reflect therefrom onto a second location of said concave surface of said concave spherical mirror (SM2) from which it reflects as a converging beam of electromagnetic radiation with an image point (FP). It is assumed in this embodiment that an effective point Source (PS) is present as a source of the beam of electromagnetic radiation (EMI).

Figure 4:
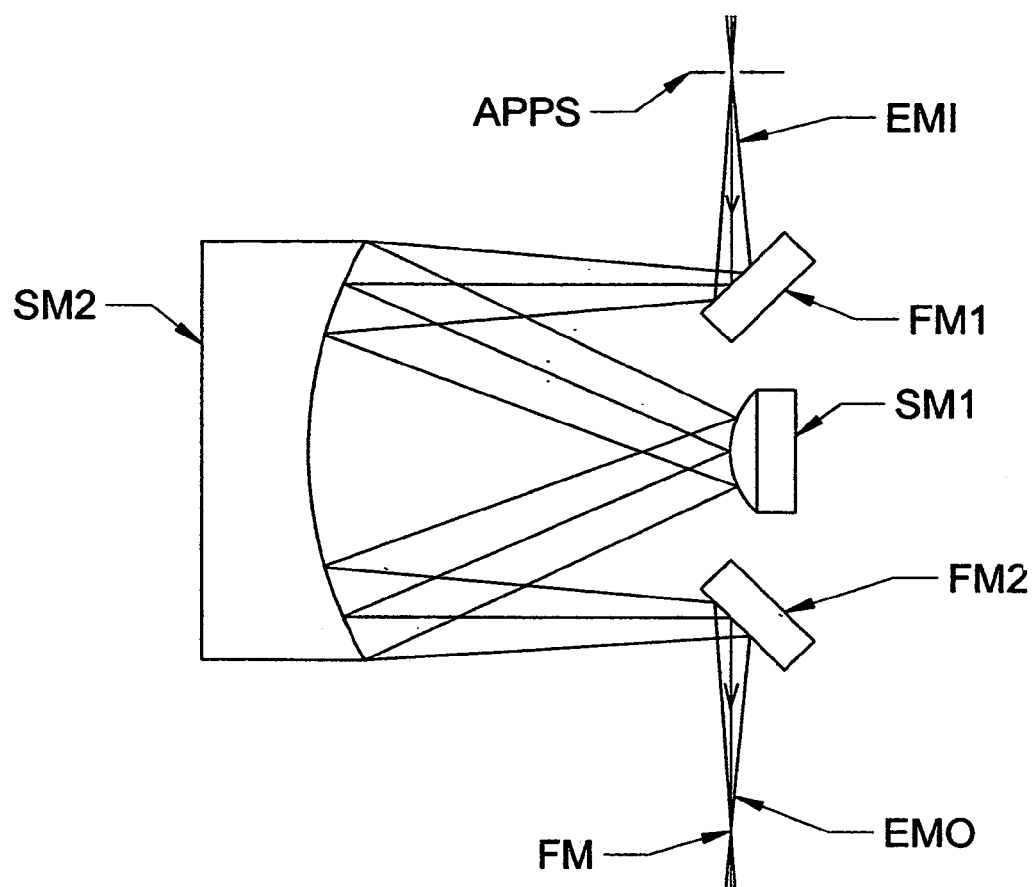
FIG. 4 shows a third embodiment of a combined present invention spatial filter and relay system.

FIG. 4 shows a combined spatial filter and relay system comprising five elements:
 a) an aperture (APPS);
 b) a first flat mirror (FM1);

c) a concave spherical mirror (SM2) having at least one concave spherical surface;

d) a convex spherical mirror (SM1) having at least one convex spherical surface; and e) a second flat mirror (FM2).

Said elements are arranged such that electromagnetic radiation (EM1) from said aperture (APPS) is caused to approach the first flat mirror (FM1) and reflect therefrom onto a first location of a concave surface of said concave spherical mirror (SM2), reflect from said first location onto a convex spherical surface of said convex spherical mirror (SM1) and reflect therefrom onto a second location of said concave surface of said concave spherical mirror (SM2) from which it reflects onto said second flat mirror (FM2) which is positioned to intercept and reflect electromagnetic radiation reflected from said second location of said concave surface of said concave spherical mirror (SM1), as a converging beam of electromagnetic radiation (EMO) with an image point (FP).

Note that the electromagnetic radiation approaches and reflects from both first flat mirror (FM1), and said second flat mirror (FM2), at 45 degree angles.

(It is noted that while said first (FM1) and second (FM2) flat mirrors are typically oriented so that a beam of electromagnetic radiation approaches along a 45 degree Angle-of-Incidence, the present invention is not limited to such a configuration. That is, said Angles-of-Incidence can be any functional angle, where, for instance, compensating adjustments are made in FIGS. 5a and 5b to effect an intended Angle-of-Incidence of the beam of electromagnetic radiation where it impinges on a Surface of said Sample (SS), and/or reflects therefrom.

Figure 5A:
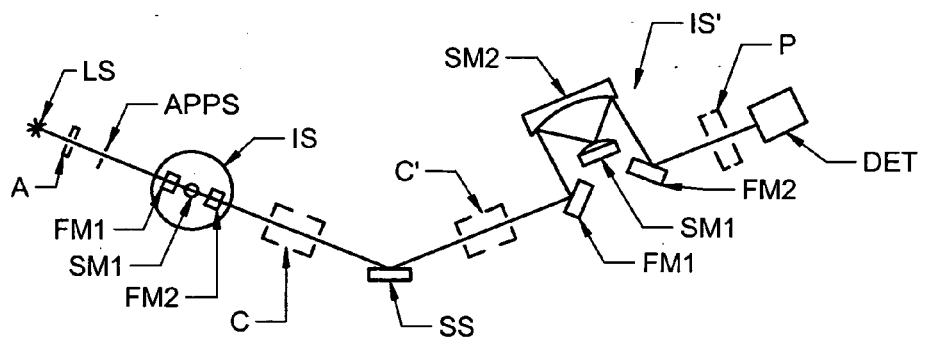
FIG. 5a show that two relay systems as shown in FIG. 4, which are rotated 90 degrees with respect to one another, can be oriented, one on the input, and one on the output side of a sample, to minimize their effect on a beam of electromagnetic radiation caused to pass therethrough.

FIG. 5a shows a present system for investigating a sample comprising:

a source of electromagnetic radiation (LS);

an aperture;

first (IS) and second (IS') relay systems, each thereof comprising four elements, as shown in FIG. 4 to be:

a) a first flat mirror (FM1);

b) a concave spherical mirror (SM2) having at least one concave spherical surface;

c) a convex spherical mirror (SM1) having at least one convex spherical surface; and d) a second flat mirror (FM2);

said elements being arranged as described with respect to FIG. 4;

and a detector (DET);

said Sample (SS) being positioned between said first and second relay systems.

Said first (IS) relay system is positioned to relay electromagnetic radiation (EMI) from the source (LS) thereof as it passes through said aperture (APPS), and direct it onto a surface of said Sample (SS) at an oblique angle of incidence, and said second (IS') relay system is positioned to receive electromagnetic radiation reflected from the Sample (SS) and pass it on to said detector (DET);

the propagation direction of electromagnetic radiation entering and exiting each of said first (IS) and second (IS') relay systems being substantially unchanged by passing therethrough;

said system being further characterized in that a plane formed by the locus of the electromagnetic radiation passing through the first (IS) relay system is oriented 90 degrees to a plane formed by the locus of the electromagnetic radiation passing through the second (IS') relay system, the purpose being to minimize effects of said first (IS) and second (IS') relay systems on a polarization state of said electromagnetic radiation which passes through both thereof.

Figure 5B:
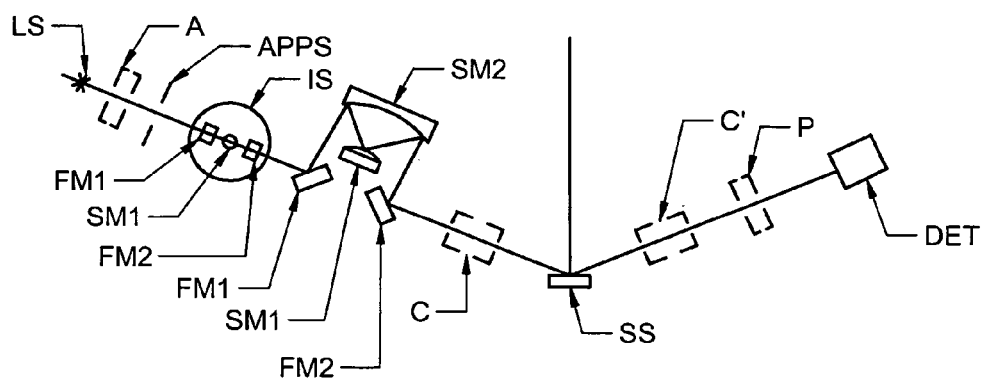
FIG. 5b shows that two relay systems as shown in FIG. 4, which are rotated 90 degrees with respect to one another, can be oriented, both on the input, (or output) side of a sample, to minimize their effect on a beam of electromagnetic radiation caused to pass therethrough.

FIG. 5b shows a variation of the FIG. 5a system for investigating a sample and comprises:

a source of electromagnetic radiation (LS);

an aperture (APPS);

first (IS) and second (IS') relay systems, each thereof comprising four elements:

a) a first flat mirror (FM1);

b) a concave spherical mirror (SM2) having at least one concave spherical surface;

c) a convex spherical mirror (SM1) having at least one convex spherical surface; and d) a second flat mirror (FM2);

and a detector. Again, both the first (IM) and second (IM') relay systems are arranged as shown in FIG. 4. Note, however, that said first (IS) and second (IS') relay systems are both positioned on the same side of the Sample (SS), as opposed what is shown in FIG. 5a. (Note, while not specifically shown, it is to be understood that both the first (IS) and second (IS') relay systems could be present after said Sample (SS)).

It is to be noted that in both FIGS. 5a and 5b, the relay systems (IS) and (IS') are oriented with respect to one another such that a plane formed by the locus of the electromagnetic radiation passing through the first (IS) relay system is oriented 90 degrees to a plane formed by the locus of the electromagnetic radiation passing through the second relay (IS') system. The purpose is to minimize effects of said first (IS) and second (IS') relay systems on a polarization state of said electromagnetic radiation which passes through both thereof.

Figure 5C:
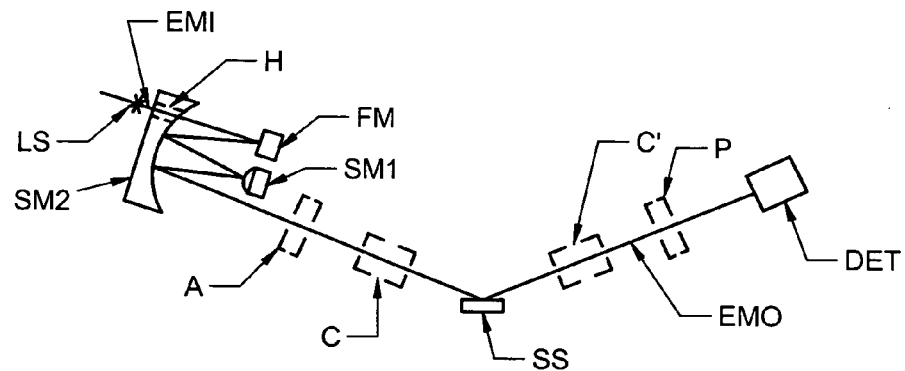
FIGS. 5c and 5d demonstrate present systems for investigating a sample.

FIG. 5c demonstrates a present system for investigating a sample comprising:

a source of electromagnetic radiation (LS);

an aperture (APPS);

a combined spatial filter and relay system comprising three elements:

a) a concave spherical mirror (SM2) having at least one concave spherical surface and an aperture hole (H) therethrough;

b) a flat mirror (FM); and c) a convex spherical mirror (SM1) having at least one convex spherical surface;

and a detector (DET).

Figure 5D:
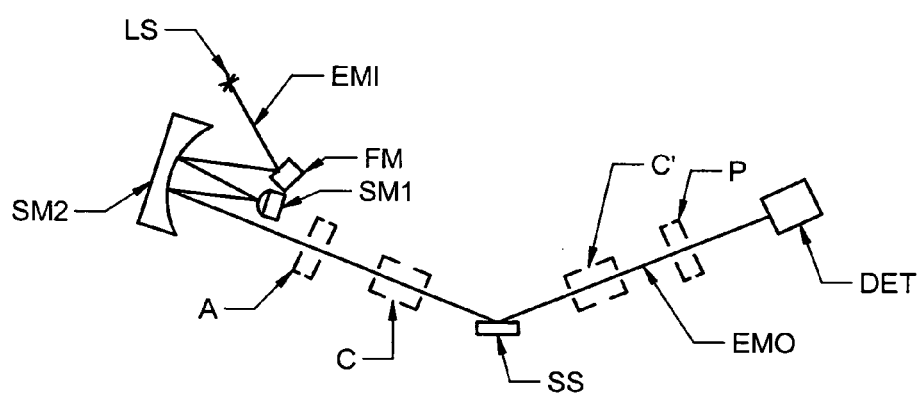

FIG. 5d demonstrates a present system for investigating a sample comprising:

a source of electromagnetic radiation (LS);

an aperture (APPS);

present invention combined spatial filter and relay system comprising:

a) an aperture (APPS);

b) a flat mirror (FM);

c) a concave spherical mirror (SM2) having at least one concave spherical surface; and d) a convex spherical mirror (SM1) having at least one convex spherical surface;

and a detector (DET).

By reference to FIGS. 5a and 5b, it should be apparent that a second combined spatial filter and relay system could be present is FIGS. 5c and 5d in a functional position and orientation. However, as the electromagnetic beam (EMI) approaches the flat mirror (FM) thereof at a more normal angle-of-incidence, it is less necessary to correct for the different effects on "P" and "S" components of said (EMI).

It is noted that in any of the FIGS. 5a-5d configurations, an optional Polarizer (P) can be placed between said Source (LS) and Sample (SS); and an optional Analyzer (A) between said Sample (SS) and Detector (DET) to form an ellipsometer system, and optional Compensators(s) (C) (C') can be placed between the Polarizer (P) and Analyzer (A) to provide a Polarimeter system. The optional components are shown in dashed lines.

Further, in all embodiments, it is to be understood that the Spatial filter Aperture (H) or (APPS) can be of a typical Circular, or of another shape. For instance, the Aperture (H) or (APPS) can be elliptical and oriented so that a beam of electromagnetic radiation passing therethrough is elongated laterally, so that as the beam impinges on the Surface of said Sample (SS) at an oblique angle, (see FIGS. 5a and 5b), which produced a longitudinally elongated result on the Surface of said Sample (SS), it defines a circular spot thereupon. FIGS. 6a and 6b demonstrate how a Circular Beam (in cross-section), appears when impinged onto the Surface of a Sample (SS) at an oblique Angle-of-Incidence. If, however, the Beam is passed through an Aperture which is not Circular, (see FIG. 6c which shows an Aperture with major and Minor Radii, (rw) and (rl), it will appear as Circular when it is impinged onto the Surface of a Sample (SS) at an oblique Angle-of-Incidence. FIG. 6d shows that a similar effect is achieved by rotating a Circular Aperture (H) or (APPS) so that a beam of electromagnetic radiation does not approach it along a perpendicular locus to a plane formed by the plate in which the Aperture (H) is present. FIGS. 6c and 6d demonstrate actually non-circular aperture and effectively non-circular aperture approaches, respectively, to making a Beam of electromagnetism non-circular prior to impinging onto the Surface of Sample (SS) at an oblique angle, so that said impinging Beam is elongated laterally. When the longitudinal lengthening then occurs, the result is a Circular Spot on the Surface of the Sample.

Figure 7A:
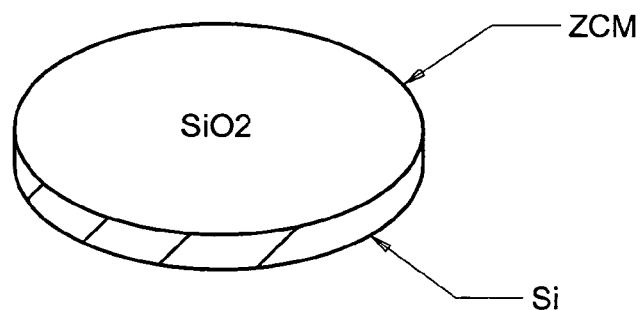
FIGS. 7a and 7b show a silicon substrate with a layer of SiO2 on a top surface thereof, and said silicon substrate with incident and reflected electromagnetic beams.
Figure 7B:
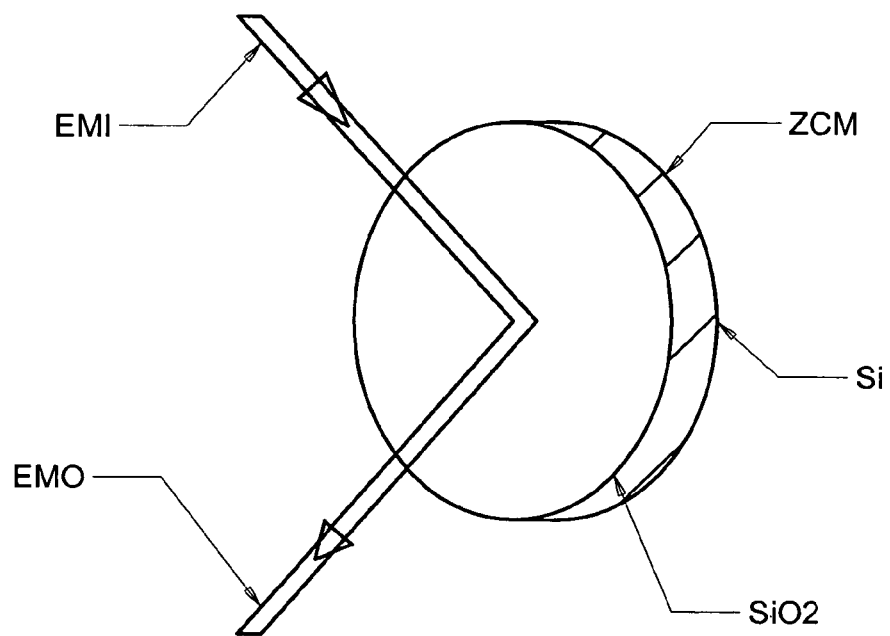
Figure 7C:
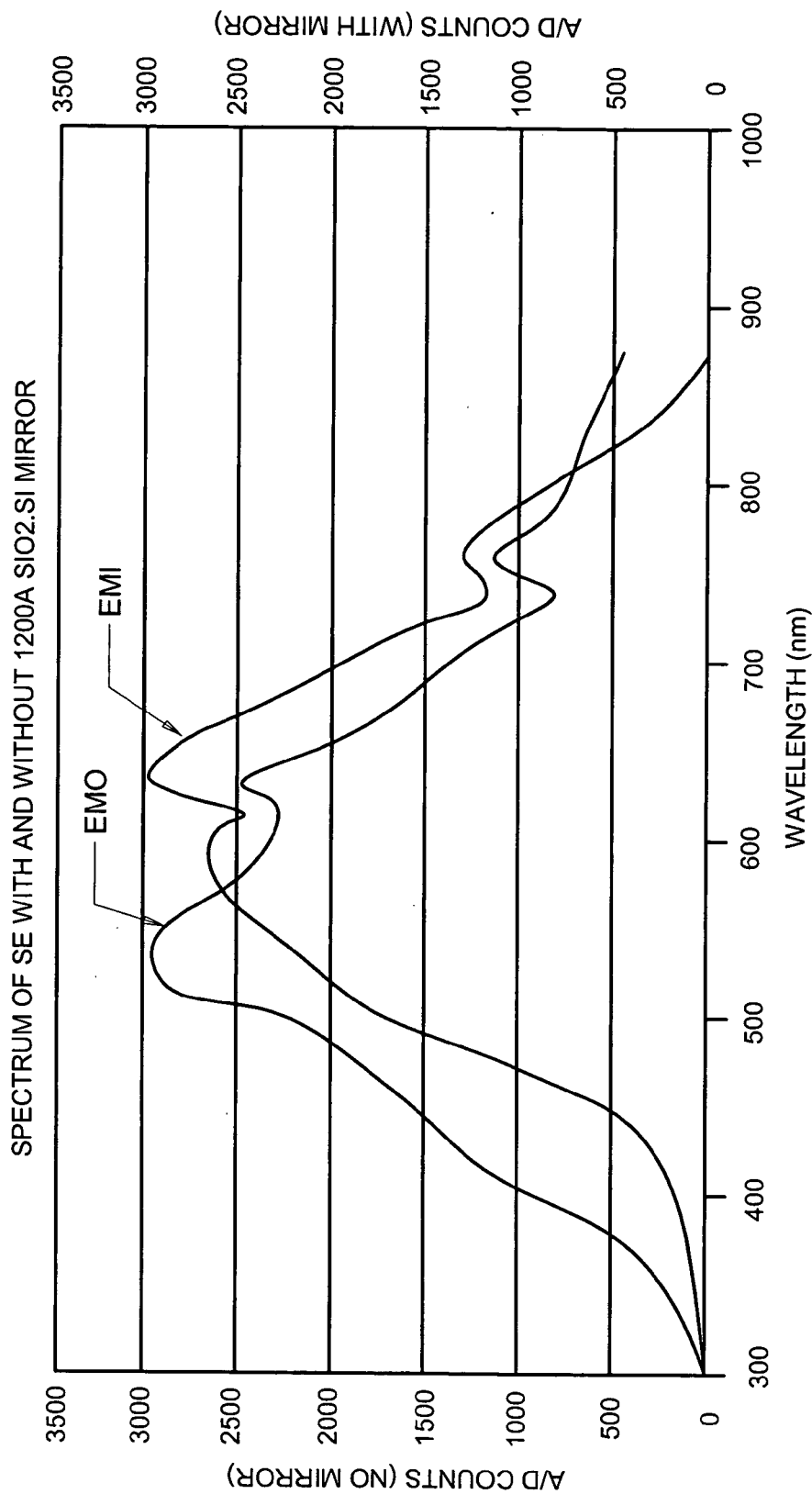
FIG. 7c demonstrates how the system of FIGS. 7a and 7b affect the relative Intensity vs. Wavelength plots of the incident and reflected beams.

It is also noted that any of the reflective surfaces, (eg. Reflective Surfaces of (FM) (when present), (SM1), (SM2) and (FM2) (when present), can be coated with a thin layer of material which alters the Energy vs. Wavelength Spectrum of the beam of electromagnetic radiation which reflects therefrom. For instance, a thin layer of SiO2 has been found to increase relative Intensity of reflected electromagnetic radiation in the IR and UV ranges, as compared to that of wavelengths in the Visible range. As a specific example of the effect a reflective surface can have on the Intensity vs. Wavelength plot of a reflected beam of electromagnetic radiation, FIGS. 7a and 7b are included to show a silicon substrate with a layer of SiO2 on a top surface thereof, and said silicon substrate with incident and reflected electromagnetic beams. FIG. 7c demonstrates how the system of FIGS. 7a and 7b affects the relative Intensity vs. Wavelength plots of the incident and reflected beams.

It is noted that the preferred relay system provides a 1:1 relationship between what is input thereto and what is output therefrom. Specifically, the preferred reflective optics in the present invention which provide electromagnetic radiation onto a sample, are not magnifying or focusing, but rather relay an effective point source of electromagnetic radiation which is, preferably an aperture which functions as a spatial filter. Said relay optics per se. are taught in an expired Patent.

Finally, it is conceived that the combined spatial filter and relay system can find application in cameras to improve depth of field.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

The invention claimed is:

1. A combined spatial filter and relay system comprising three elements:
    a) a concave spherical mirror having at least one concave spherical surface and an aperture hole therethrough;
    b) a flat mirror; and
    c) a convex spherical mirror having at least one convex spherical surface;
said elements being arranged such that electromagnetic radiation caused to approach the concave spherical mirror passes through said aperture hole thereby forming an effective point source of electromagnetic radiation thereat, then proceeds as an expanding electromagnetic beam and reflects from said flat mirror onto a first location of a concave surface of said concave spherical mirror, then reflects from said first location onto a convex spherical surface of said convex spherical mirror and reflects therefrom onto a second location of said concave surface of said concave spherical mirror from which it reflects as a converging beam of electromagnetic radiation.

2. A system for investigating a sample as in claim 1 which further comprises a coating on at least one of the concave, convex and flat mirrors which changes the intensity vs. wavelength plot of a reflected electromagnetic beam relative to an incident beam.

3. A system for investigating a sample as in claim 1, in which said aperture hole is actually or effectively non-circular.

4. A combined spatial filter and relay system comprising:
    a) an aperture;
    b) a flat mirror;
    c) a concave spherical mirror having at least one concave spherical surface; and
    d) a convex spherical mirror having at least one convex spherical surface;
said elements being arranged such that electromagnetic radiation caused to approach from said aperture forms an effective point source of electromagnetic radiation thereat, then proceeds as an expanding electromagnetic beam and is caused to approach the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation.

5. A combined spatial filter and relay system as in claim 4, which further comprises a second flat mirror positioned to intercept and reflect electromagnetic radiation reflected from said second location of said concave surface of said concave spherical mirror as a converging beam of electromagnetic radiation.

6. A system for investigating a sample as in claim 4 which further comprises a coating on at least one of the concave, convex and flat mirrors which changes the intensity vs. wavelength plot of a reflected electromagnetic beam relative to an incident beam.

7. A system for investigating a sample as in claim 4, in which said aperture is actually or effectively non-circular.

8. A combined spatial filter and relay system comprising five elements:
   a) an aperture;
   b) a first flat mirror;
   c) a concave spherical mirror having at least one concave spherical surface;
   d) a convex spherical mirror having at least one convex spherical surface; and
   e) a second flat mirror;

said elements being arranged such that electromagnetic radiation caused to approach said aperture forms an effective point source of electromagnetic radiation thereat, then proceeds as an expanding electromagnetic beam and is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation.

9. A combined spatial filter and relay system as in claim 8 wherein electromagnetic radiation from said aperture is caused to approach the first flat mirror at a 45 degree angle, and reflect from said second flat mirror at a 45 degree angle.

10. A system for investigating a sample as in claim 8 which further comprises a coating on at least one of the concave, convex, first flat and second flat mirrors which changes the intensity vs. wavelength plot of a reflected electromagnetic beam relative to an incident beam.

11. A system for investigating a sample as in claim 8, in which said aperture is actually or effectively non-circular.

12. A system for investigating a sample comprising:
a source of electromagnetic radiation;
an aperture;
first and second relay systems, each thereof comprising four elements:
   a) a first flat mirror;
   b) a concave spherical mirror having at least one concave spherical surface;
   c) a convex spherical mirror having at least one convex spherical surface; and
   d) a second flat mirror;
said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation;
and a detector;
said sample being positioned between said first and second relay systems;
said first relay system being positioned to relay electromagnetic radiation from the source thereof, as it passes through said aperture, and direct it onto a surface of said sample at an oblique angle of incidence, and said second relay system being positioned to receive electromagnetic radiation reflected from the sample and pass it on to said detector;
the propagation direction of electromagnetic radiation entering and exiting each of said first and second relay systems being substantially unchanged by passing therethrough;
said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

13. A system for investigating a sample as in claim 12 which further comprises:
   a) a polarizer between said source and sample; and
   b) an analyzer between said sample and detector;
wherein said system is an ellipsometer.

14. A system for investigating a sample as in claim 13 which further comprises at least one compensator between said source and detector.

15. A system for investigating a sample as in claim 12 which further comprises a coating on at least one of the concave, convex, first flat and second flat mirrors which changes the intensity vs. wavelength plot of a reflected electromagnetic beam relative to an incident beam.

16. A system for investigating a sample as in claim 12, in which said aperture is actually or effectively non-circular.

17. A system for investigating a sample comprising:
a source of electromagnetic radiation;
an aperture;
first and second relay systems, each thereof comprising four elements:
   a) a first flat mirror;
   b) a concave spherical mirror having at least one concave spherical surface;
   c) a convex spherical mirror having at least one convex spherical surface; and
   d) a second flat mirror;
said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation;
and a detector;
said first and second relay systems being positioned on the same side of the sample;
the propagation direction of electromagnetic radiation entering and exiting each of said first and second relay systems being substantially unchanged by passing therethrough;
said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

18. A system for investigating a sample as in claim 17 which further comprises:
 a) a polarizer between said source and sample; and
 b) an analyzer between said sample and detector;
wherein said system is an ellipsometer.

19. A system for investigating a sample as in claim 18 which further comprises at least one compensator between said source and detector.

20. A system for investigating a sample as in claim 17 which further comprises a coating on at least one of the concave, convex, first flat and second flat mirrors which changes the intensity vs. wavelength plot of a reflected electromagnetic beam relative to an incident beam.

21. A system for investigating a sample as in claim 17, in which said aperture is actually or effectively non-circular.

22. A system for investigating a sample comprising:
a source of electromagnetic radiation;
an aperture;
a relay system comprising three elements:
 a) a flat mirror;
 b) a concave spherical mirror having at least one concave spherical surface;
 c) a convex spherical mirror having at least one convex spherical surface;
said elements being arranged such that electromagnetic radiation is caused to approach said aperture and form an effective point source of electromagnetic radiation thereat, then proceed as an expanding electromagnetic beam toward the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation;
a sample; and
a detector.

23. A system for investigating a sample as in claim 22 in which said aperture is in said concave spherical mirror.

24. A system for investigating a sample as in claim 22 which further comprises:
 a) a polarizer between said source and sample; and
 b) an analyzer between said sample and detector;
wherein said system is an ellipsometer.

25. A system for investigating a sample as in claim 22 which further comprises at least one compensator between said source and detector.

26. A system for investigating a sample as in claim 22 which further comprises a coating on at least one of the concave, convex, first flat and second flat mirrors which changes the intensity vs. wavelength plot of a reflected electromagnetic beam relative to an incident beam.

27. A system for investigating a sample as in claim 22, in which said aperture is actually or effectively non-circular.

* * * * *